United States Patent
Plassky et al.

(10) Patent No.: US 7,670,345 B2
(45) Date of Patent: Mar. 2, 2010

(54) USER GUIDANCE IN ADJUSTING BONE INCISION BLOCKS

(75) Inventors: Norman Plassky, Erfurt (DE); Timo Neubauer, Feldkirchen (DE); Christian Brack, Diedorf (DE); Hubert Götte, Munich (DE)

(73) Assignee: BrainLAB AG, Feldkirchen (DE)

( * ) Notice: Subject to any disclaimer, the term of this patent is extended or adjusted under 35 U.S.C. 154(b) by 366 days.

(21) Appl. No.: 11/354,578

(22) Filed: Feb. 15, 2006

(65) Prior Publication Data
US 2006/0217733 A1 Sep. 28, 2006

Related U.S. Application Data

(60) Provisional application No. 60/655,584, filed on Feb. 23, 2005.

(30) Foreign Application Priority Data

Feb. 15, 2005 (EP) .................... 05003148

(51) Int. Cl.
*A61F 2/00* (2006.01)
(52) U.S. Cl. ....................................... 606/88
(58) Field of Classification Search ........... 606/86 R, 606/87–89
See application file for complete search history.

(56) References Cited

U.S. PATENT DOCUMENTS

| | | | |
|---|---|---|---|
| 6,551,325 B2 * | 4/2003 | Neubauer et al. | 606/88 |
| 7,029,477 B2 * | 4/2006 | Grimm | 606/88 |
| 2002/0068942 A1 | 6/2002 | Neubauer et al. | |
| 2002/0198531 A1 | 12/2002 | Millard et al. | |
| 2005/0075632 A1 * | 4/2005 | Russell et al. | 606/53 |

FOREIGN PATENT DOCUMENTS

| | | |
|---|---|---|
| DE | 202 02 615 U1 | 6/2002 |
| DE | 203 03 643 U1 | 7/2003 |
| DE | 1 430 842 A | 6/2004 |
| WO | 2004/019792 A | 3/2004 |

OTHER PUBLICATIONS

English translation of Aesculap AG & Co. KG (DE 202 02 615 U1), "Template to Guide a Surgical Cutting Tool", 2002.

* cited by examiner

*Primary Examiner*—Eduardo C Robert
*Assistant Examiner*—Ellen C Hammond
(74) *Attorney, Agent, or Firm*—Renner, Otto, Boisselle & Sklar, LLP

(57) ABSTRACT

A bone incision block includes an incision guide, a localization reference adjustably attached to the incision guide, a fastener for fastening to a bone, and an adjustment device. The incision guide defines an incision plane, and the localization reference enables the incision plane to be spatially determined. The adjustment device is operatively coupled between the fastener and the incision guide, wherein the incision plane can be set relative to the bone via the adjustment device, and a spatial position of the adjustment device can be determined via a registration element.

15 Claims, 15 Drawing Sheets

USER GUIDANCE IN ADJUSTING BONE INCISION BLOCKS

RELATED APPLICATION DATA

This application claims priority of U.S. Provisional Application No. 60/655,584 filed on Feb. 23, 2005, which is incorporated herein by reference in its entirety.

FIELD OF THE INVENTION

The invention relates to adjusting bone incision blocks and, more particularly, to a system and method for guiding a user in adjusting the bone incision block.

BACKGROUND OF THE INVENTION

In computer-assisted knee arthroplasty, for example, an incision block is commonly used, wherein the incision block includes an incision guide for defining an incision plane. A localization reference is attached to the incision guide, wherein the localization reference can be spatially adjusted, e.g., rotated, in order to allow the localization reference to be optimally visible for various applications and/or configurations. By means of the localization reference and a medical navigation system, an attempt is made to position the incision block such that the incision guide comes to rest in a planned incision plane.

A guiding block for use in surgical incisions is known from WO 2004/017843 A1, including a fixation part that is fastened to a bone, and a guiding part that can be moved relative to the fixation part and adjusted in its position. Light-emitting diodes are used to indicate the position of the guiding part. DE 102 07 035 A1 discloses a template for guiding a surgical treatment tool, including a fastening means for fixing the template to a bone to be treated via three bone screws.

An adjustment means can be used to set the incision plane in the 'slope', 'varus-valgus' and 'resection depth' degrees of freedom typical for bones, in accordance with the presets of the navigation system (target incision plane). However, this can be problematic when the bone incision block (in particular the adjustment means) is fastened to the bone such that the operating elements are not clearly assigned to the degrees of freedom of the incision plane defined by the incision guide. In such cases, for example, operating an element may result in a change in more than one degree of freedom, or two operating elements may need to be activated in order to adjust in one degree of freedom. Finding the most favorable way to complete the adjusting process in the shortest period of time then depends largely on the knowledge and experience of the operator. Although the target incision plane is preset by navigation, it is often difficult to set the incision guide in accordance with target incision plane and/or presets without assistance, especially if the incision block is arranged unfavorably on the bone. If unfavorably arranged on the bone, an iterative procedure may be necessary, since direct adjusting using the interdependence of the functional members is not possible.

SUMMARY OF THE INVENTION

A settable bone incision block is provided that advantageously includes a registration element, wherein the registration element can be used to determine a spatial position of an adjustment device. In other words, the registration element can ensure that the position of the adjustment device on the bone can be ascertained, which occasionally also presupposes information on the position of the localization reference. If the position and orientation of the adjustment device on the bone are known, then it is possible to predict the effect that the settings of the adjustment device will have on the incision plane of the incision guide. With this knowledge, it is possible to assist the user such that he may quickly and exactly set the incision guide.

The settable incision block including these registration features and adjustment device, in combination with a software algorithm and a user interface, allow the necessary setting movements to be exactly determined and provided to the user. This can be performed for any arrangement of the incision block on the bone (anterior-posterior, medial, lateral, . . . ). For example, since the structure of the bone incision block (in particular, the adjustment device) is known (e.g. stored in the navigation system), and the position of the adjustment device can be ascertained with respect to the bone axis and bone planes, it is possible to calculate in what way the adjustment device should be activated in order to set the incision plane defined by the incision guide so as to correspond to the target incision plane.

In other words, the target incision plane has hitherto been indicated on a screen display, but the path to achieve the incision plane has not been provided. If the incision block arrangement is unfavorable, the user, without guidance, cannot intuitively predict the effect that a particular manipulation of the adjustment device will have on the resulting incision plane. By guiding the user while he operates the adjusting device, a settable bone incision block can be easily used in all possible arrangements (e.g., fastened around the whole leg). In standard anterior arrangements, it is not difficult to exactly assign a setting medium to a desired degree of freedom.

An advantage of the invention is that the spatial position of the adjustment device can be determined such that the user is provided with the actual incision plane (e.g., the plane defined by the incision guide), the target incision plane (e.g., the target plane as determined by the navigation system), the difference between the two, and instructions as to how he can set the actual incision plane to correspond with the target incision plane (e.g., instructions on how to manipulate the adjustment device). This user guidance can be used in all possible arrangements of the incision block around the bone, and can save time and yet allow the incision plane to be set exactly.

The adjustment device can include setting media (also referred to as a setting device) by means of which the incision guide can be rotated around two non-parallel axes and adjusted in height. One setting medium, e.g., hand wheel screw setting devices, can be provided for each degree of freedom.

The registration element can include an at least puncticular reference arranged fixed to the adjustment device. It is possible to arrange the reference of the adjustment device at a location characteristic of the individual bone incision block. The possibility also exists of arranging the reference of the adjustment device at a preset distance from the localization reference or, for various configurations (various arrangements of the incision guide with respect to the adjustment device), at a defined presettable distance from the localization reference.

The reference can be a depression at a point on the surface of the adjustment device, e.g., a "one-dimensional" puncticular reference. In the registration process, a navigated pointer, for example, can be moved to such a depression to determine its position (navigation system).

The reference also can have a two-dimensional extent and, in particular, can be a bore at a point on the adjustment device or can have two depressions on the surface of the adjustment device, wherein the spatial position of the two-dimensional elements can be detected in the registration process using a navigated pointer.

In another embodiment, the spatial position of the adjustment device can be set, predetermined with respect to the localization reference, wherein a locking interface provided between the adjustment device (including its registration element) and the incision guide (including its localization reference) only allows defined relative positions of the two elements, the corresponding information being stored in the navigation system.

The method for user guidance in setting the incision plane of the incision guide of a bone incision block using an incision guide adjustment device can include the following steps:
  defining a target incision plane;
  spatially determining an actual incision plane with the aid of a medical navigation system and a localization reference which is attached to the incision guide;
  determining the spatial position of the adjustment device with respect to the bone by means of a registration element; and
  outputting adjustment instructions, depending on the spatial position of the adjustment device, which, starting from the actual incision plane, assist the user in setting the target incision plane.

The method can be performed using a bone incision block such as has been described above. It is particularly advantageous if the adjustment instructions for individual setting media of the adjustment device are output by means of a screen output, in particular the screen output of the navigation system. Such an image output can be complemented by an acoustic output. Marking the setting media in color or in other ways (e.g., numbering) also facilitates setup, since clearly identifying the setting media to be currently used via a corresponding screen output can make it easier for the user to locate them on the incision block.

BRIEF DESCRIPTION OF THE DRAWINGS

The forgoing and other embodiments of the invention are hereinafter discussed with reference to the drawings.

DETAILED DESCRIPTION

Figure 1:
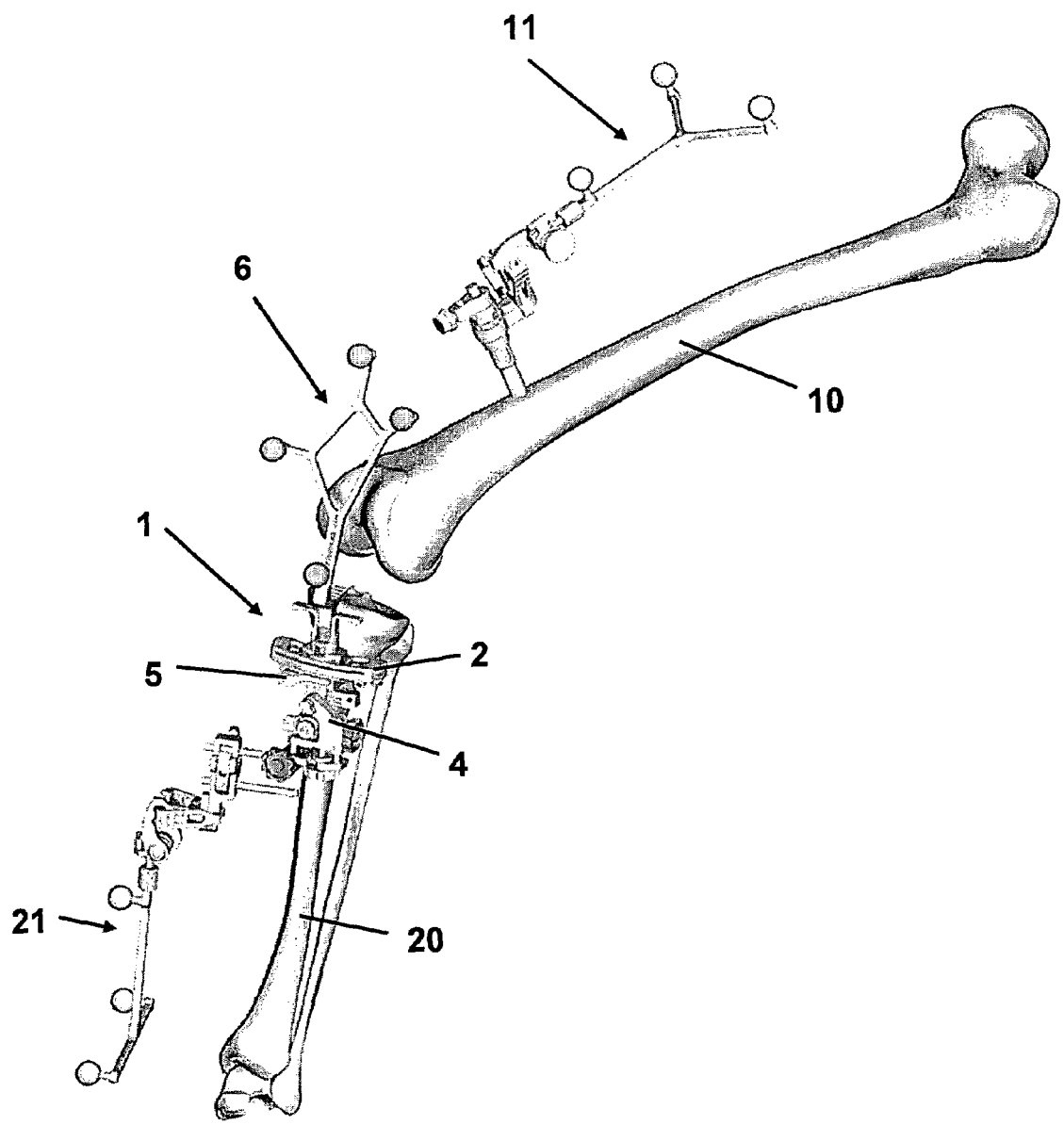
FIG. 1 illustrates an exemplary arrangement of an incision block on the lower leg bone, wherein the incision block is in the navigated range of a navigation system.

FIG. 1 shows the range in which a bone incision block 1 is used while a user guidance method is performed. The individual components of the bone incision block 1 can be seen more clearly in FIG. 2. The bone incision block 1 is fastened to a lower leg bone 20 via its fastener 3 (FIG. 2), and in particular screwed on or held by Schanz screws, Kirschner wires or similar fastening media. The adjustment device 4 is connected to the fastener 3 and the incision guide 2 is fixed to the adjustment device 4. The localization reference 6 is rotatably arranged on top of the incision guide 2 and bears a group of reflective markers.

In FIG. 1, it can also be seen that a reference 21 is provided on the lower leg bone 20 and another reference 11 is provided on the upper leg bone 10. The bones and incision guide 2 are thus localized and navigated, using a navigation system (FIG. 17) that can comprise two tracking cameras, an infrared light source, a computer data processing system and a screen output. In particular, a VektorVision® system from the company BrainLAB can be used as the navigation system.

Figure 2:
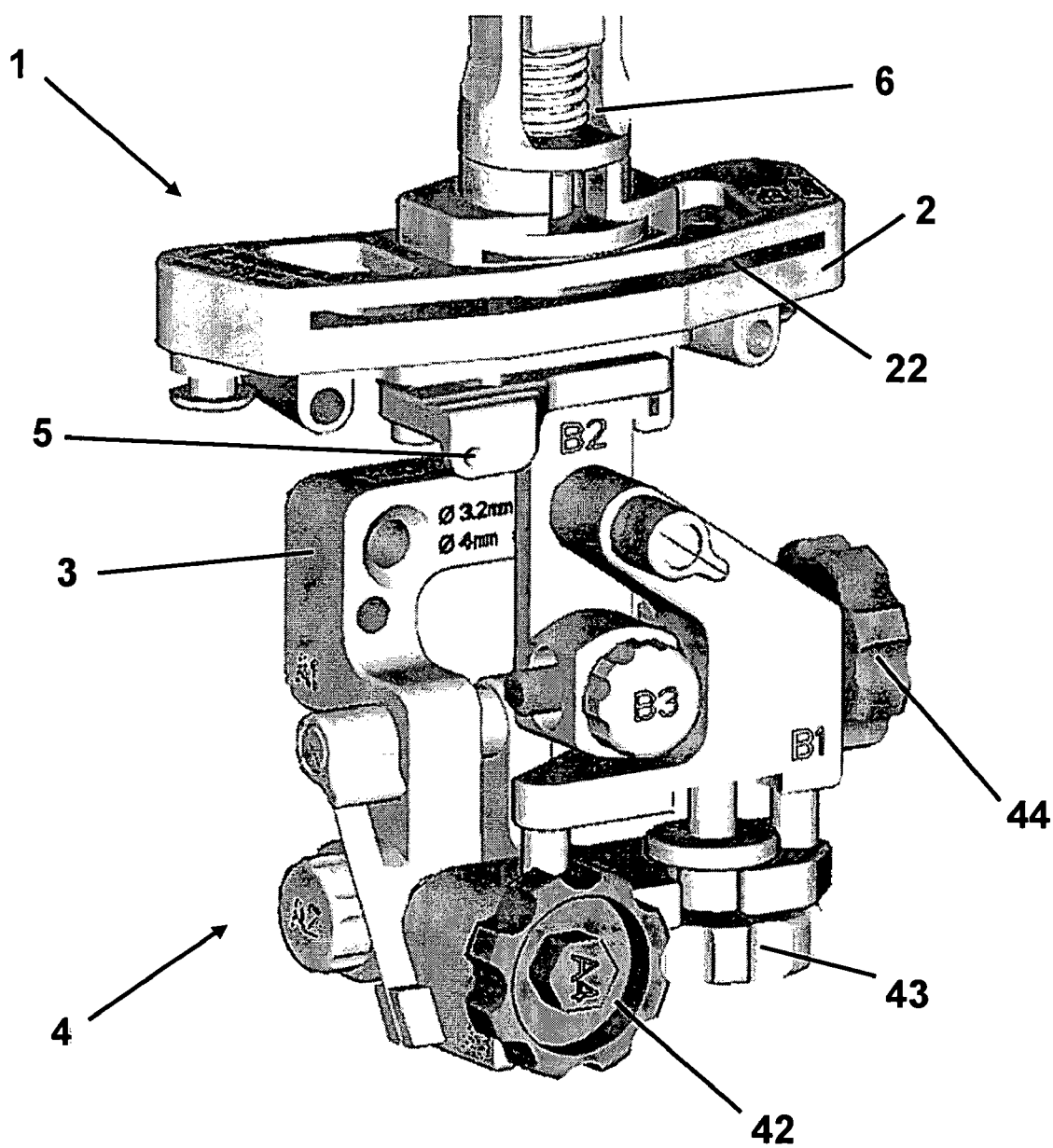
FIG. 2 an enlarged representation of an exemplary incision block including a one-dimensional registration element.

In FIG. 2, it can be seen that the incision guide 2 comprises a guiding slit 22 for a surgical tool, e.g., a saw. The localization reference 6 is rotatably attached to the incision guide 2 such that it can be aligned, is unobtrusive, and is easily visible to the navigation system (camera tracking unit). Because the localization reference 6 can be rotated, it cannot provide the navigation system with the exact position of the adjustment device 4, but it can provide the position of the incision plane (incision guide) formed by the slit 22.

In order to provide user guidance, it is necessary to know the spatial position of the adjustment device 4 (especially with respect to the bone to be treated). In a first embodiment, this purpose is served by the registration point 5, which is embodied as a depression at the top end of the adjustment device 4. The tip of a navigable pointer, for example, can be inserted into such a depression to determine the spatial position of the depression 5 (and therefore the adjustment device 4) using the navigation system. The information thus obtained, combined with the information on the position of the localization reference 6, is sufficient to determine the position of the adjustment device on the bone. Based on this information, instructions for the setting process (i.e., for reaching the target incision plane) are derived.

The adjustment device 4 has three hand wheels 42, 43 and 44 using which the incision guide 2 can be tilted around two non-parallel axes and adjusted in height. Therefore, all the inclination positions for the incision plane within the adjusting range of the adjustment device 4 as defined by the mechanism in principle can be reached. In order to adjust the bone incision block 1, the user completes the following method steps:

First, the leg is registered in the navigation system, by means of the references 11 and 21 for the bones 10 and 20 (FIG. 1). Thus, the characteristic axes and planes of the leg can be calculated by the navigation system. The hand wheels 42, 43 and 44 of the adjustment device 4 are set to their zero values beforehand, in order to provide a maximum setting range in all directions and degrees of freedom.

Figure 6:
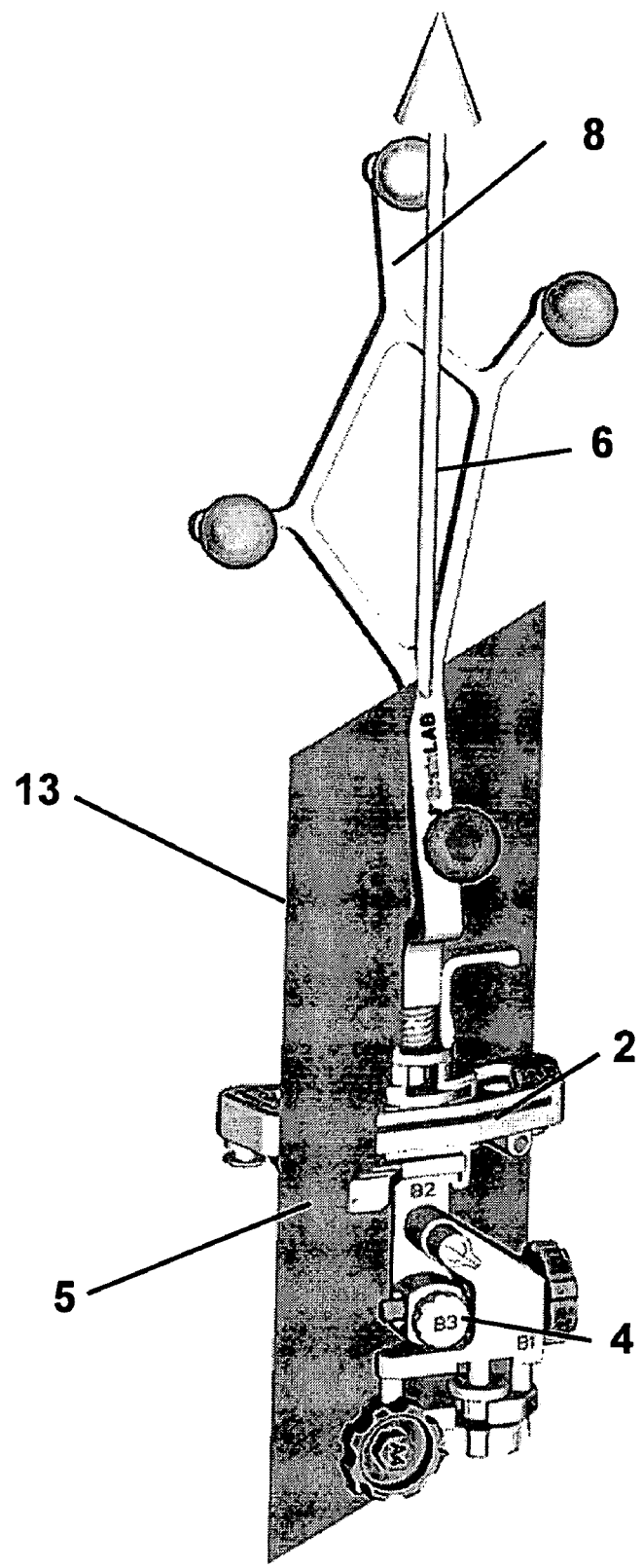
FIG. 6 illustrate an exemplary incision block with a registration plane mounted through the rotational axis of the localization reference and the registration point (one-dimensional registration element).
Figure 7:
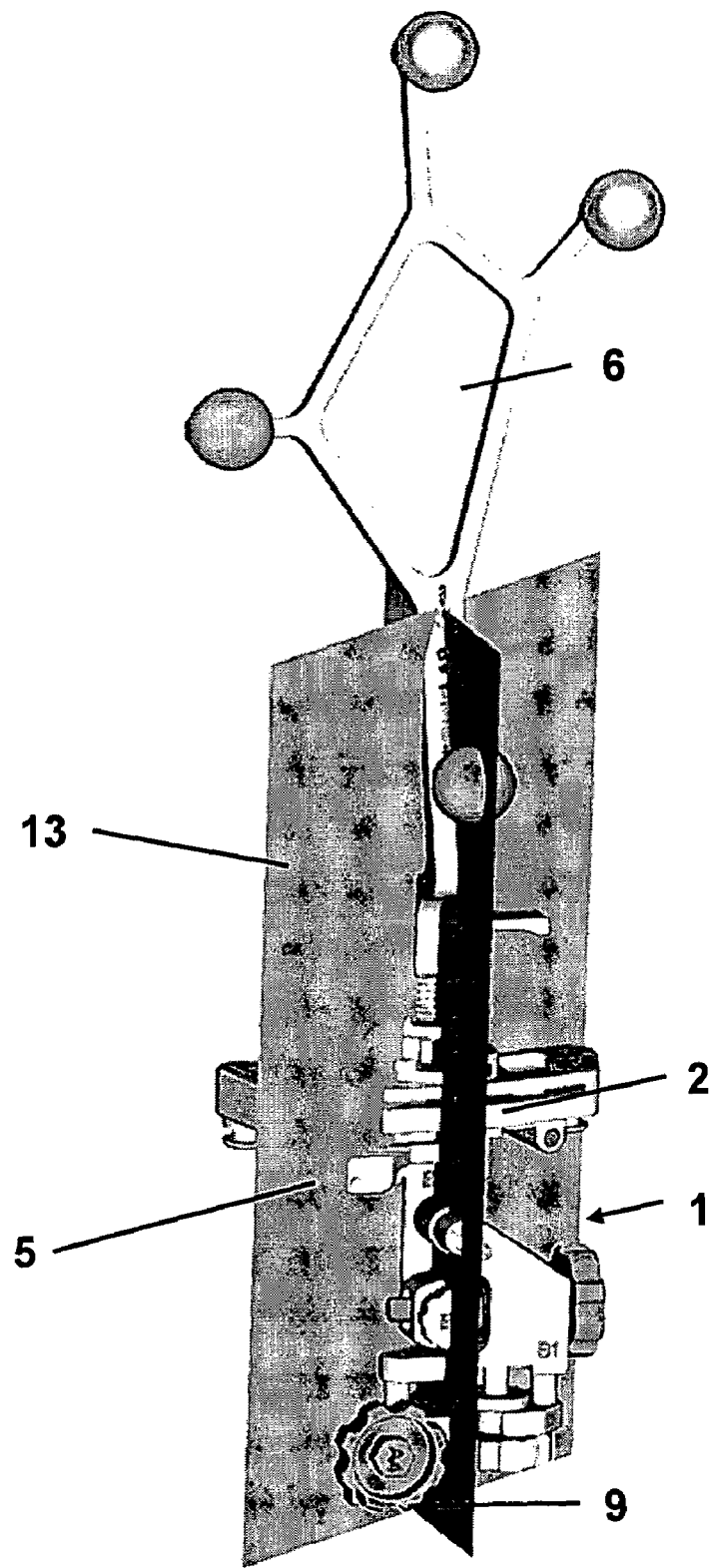
FIG. 7 illustrates an exemplary incision block showing the registration plane and plane of symmetry of the adjustment device and their relationship to one another.
Figure 8:
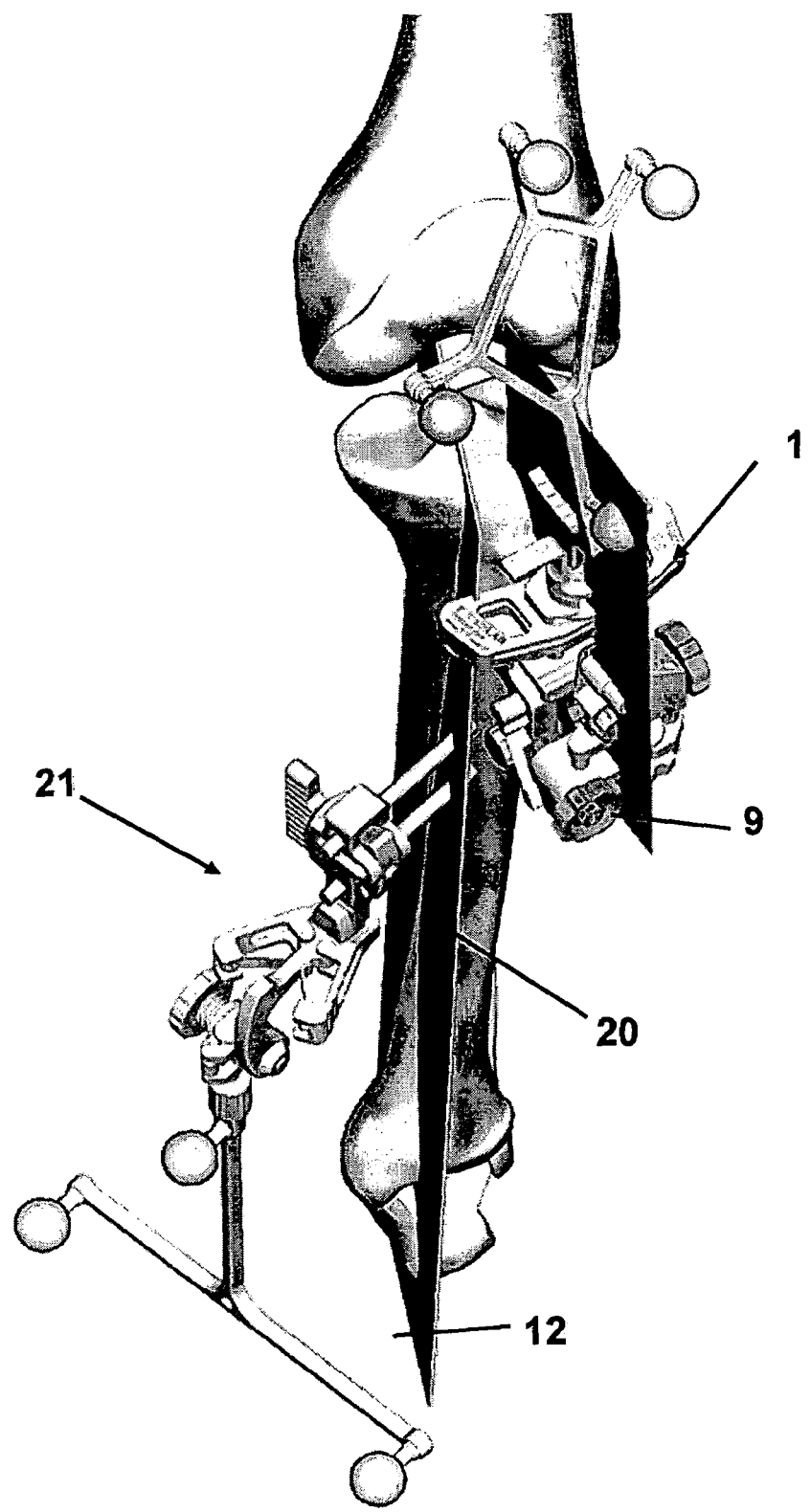
FIG. 8 illustrates an exemplary incision block (with the plane of symmetry of the adjustment device shown) fastened to the lower leg (with the sagittal plane shown).

If multiple configurations are possible for the position of the incision guide 2 relative to the adjustment device 4, then the incision guide 2 is mounted in the desired position on the adjustment device 4. By way of explanation, reference is made here to FIGS. 3 to 5, which each show different positions of the incision guide 2 relative to the adjustment device 4. The arrows 7 indicate different distances (stored as values in the navigation system) between a selected but fixed point on the incision guide 2, which ideally passes through the rotational axis of the localization reference, and the registration point 5. Thus, when such different configurations are possible (as, for example, in accordance with FIGS. 3 to 5), the assisting navigation system has to be informed of the relationship of the localization reference 6 to the adjustment device 4, by ascertaining the distance between the axis of the rotatable localization reference 6 and the registration point 5. Because the localization reference 6 can be rotated, the additional registration point 5 is necessary in order to establish the registration plane 13 which, for the different configurations (FIGS. 3 to 5), has different angles with respect to the plane of symmetry of the incision block. The registration plane 13 is shown in FIG. 6, and the arrow with the reference sign 8 indicates the rotational axis of the localization reference 6. FIG. 7 then shows the difference between the registration plane 13 and the plane of symmetry 9 of the bone incision block 1.

Figure 3:
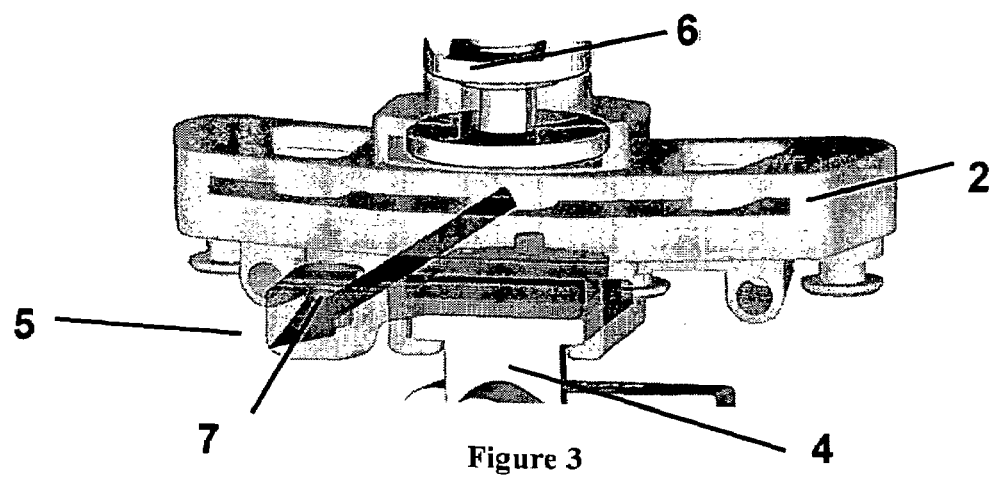
FIGS. 3-5 illustrate various exemplary incision guide configurations and/or arrangements of the incision guides on an incision block.
Figure 4:
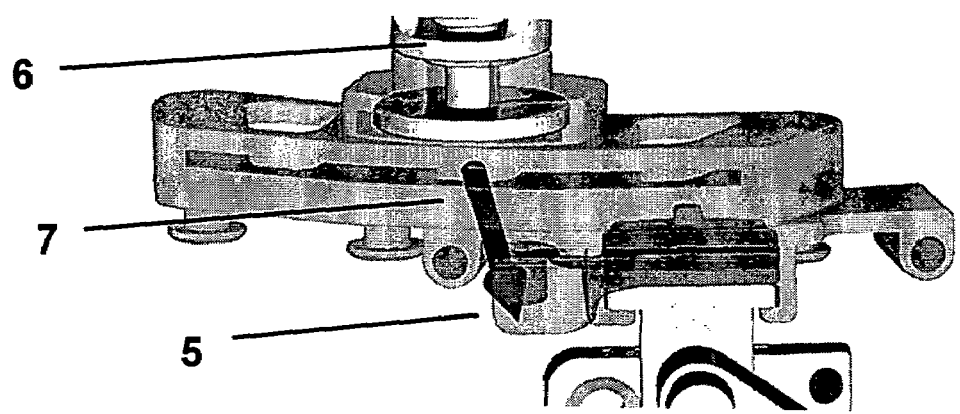
Figure 5:
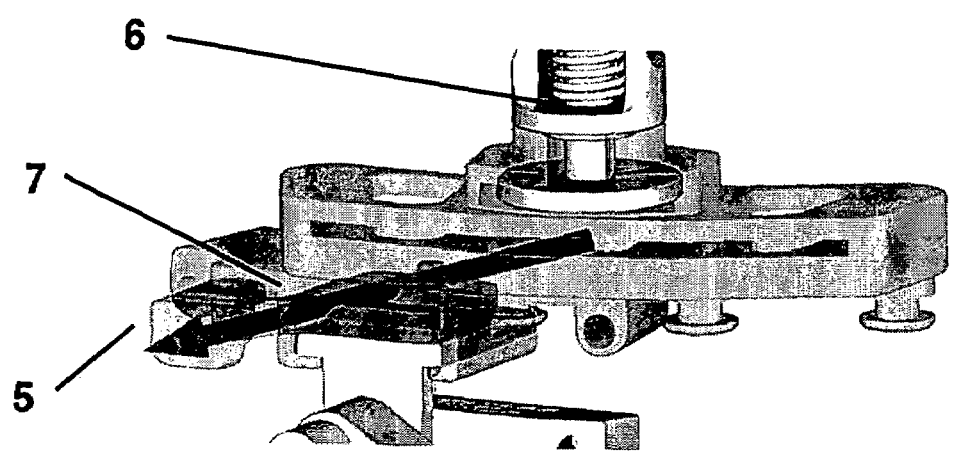

The particular arrow length for the arrow 7 in FIGS. 3 to 5 is then used to find the coordination angle between the registration plane 13 and the plane of symmetry 9 of the bone incision block which is stored in the data set of the navigation system.

When the incision guide 2 and the adjustment device 4 are connected to one another in a desired configuration, the localization reference 6 is attached to the incision guide 2. When assembled, the bone incision block 1 can be placed (e.g., screwed) onto the bone at any point near the resection area. The bone incision block 1 and/or the adjustment device 4 (and the incision guide 2 which in this embodiment is fixedly connected to it) are then registered, e.g., by identifying the registration point 5 with a navigated pointer, the tip of which comes to rest in the depression.

If various configurations, i.e., relative positions between the incision guide 2 and the adjustment device 4, are possible (FIGS. 3 to 5), then the distance between the axis of the localization reference 6 and the registration point 5 is calculated. These distances are correlated with the angle between the registration plane 13 and the plane of symmetry 9 of the incision block previously stored in the database.

Using the planes calculated as described above (registration plane 13, plane of symmetry 9), it is then possible to calculate the position of the incision block 1 (in particular, the position of the adjustment device 4) on the bone using software, wherein the plane of symmetry 9 calculated is compared with the sagittal plane of the bone. FIG. 7 shows the difference between the plane of symmetry 9 of the incision block 1 and the sagittal plane of the bone to be treated. The proportions for the settings on the hand wheels 42, 43 and 44 of the adjustment device 4 then can be calculated and output to the user, for example, on the screen of the navigation system. The output can indicate which wheel is to be rotated (e.g., by color coding) until a stop signal occurs, such that the target incision plane can be set in only three steps. The software algorithm takes into account the interacting degrees of freedom and exactly calculates the values for adjusting in the individual degrees of freedom so as to transition the actual incision plane into the target incision plane. In the first or second setting step, one of the incision plane parameters may not necessarily obtain its target value, which makes suppressing the characteristic values during user guidance useful, so as not to confuse the user with the readings which occasionally deviate from the target value. One favorable user guidance is to display the setting medium to be activated (which can for example be distinguished according to color) until its target value is reached. This process is repeated until all the necessary manipulations of the adjustment device have been performed. The result is then displayed as a comparison between the target incision plane and the actual incision plane.

Figure 9:
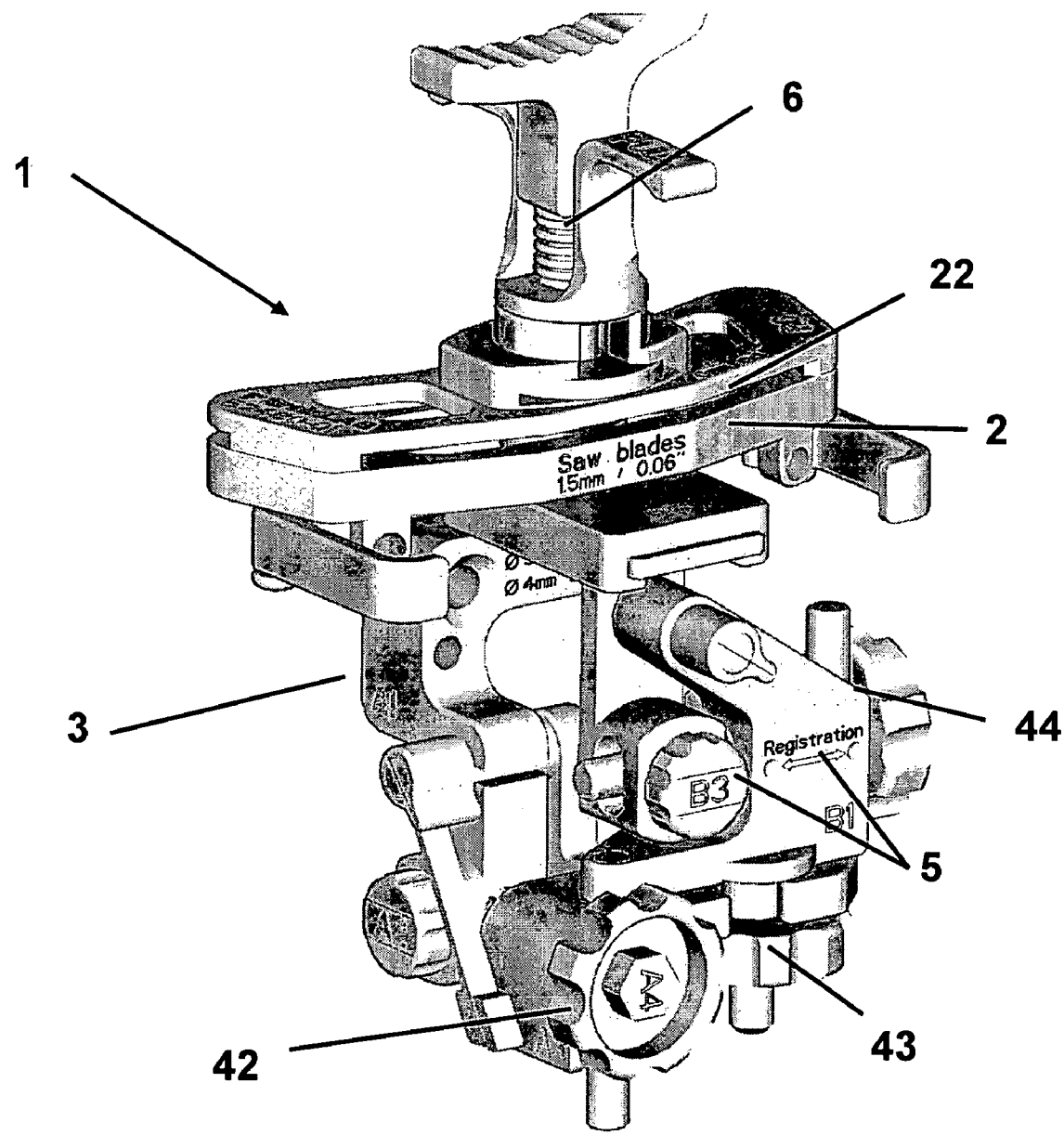
FIG. 9 illustrates an enlarged representation of an exemplary incision block with a two-dimensional registration element.

FIG. 9 shows a second embodiment of the incision block, wherein a two-dimensional registration element 5 is provided. The two-dimensional registration element 5 is useful when pre-defined configurations between the adjustment device 4 and the incision guide 2 are not provided or not possible. In such situations, correlations via characteristic distances 7 and angular relationships (which are stored in the database) cannot be performed. Using two-dimensional registration elements allows the incision guide 2 to move freely within the incision plane, wherein the information regarding the incision plane is provided as usual to the navigation system via the localization reference 6. Additionally, the position of the adjustment device on the bone is determined with the aid of the two-dimensional registration element 5 (e.g. two points or a bore forming the normal vector of a plane).

Figure 10:
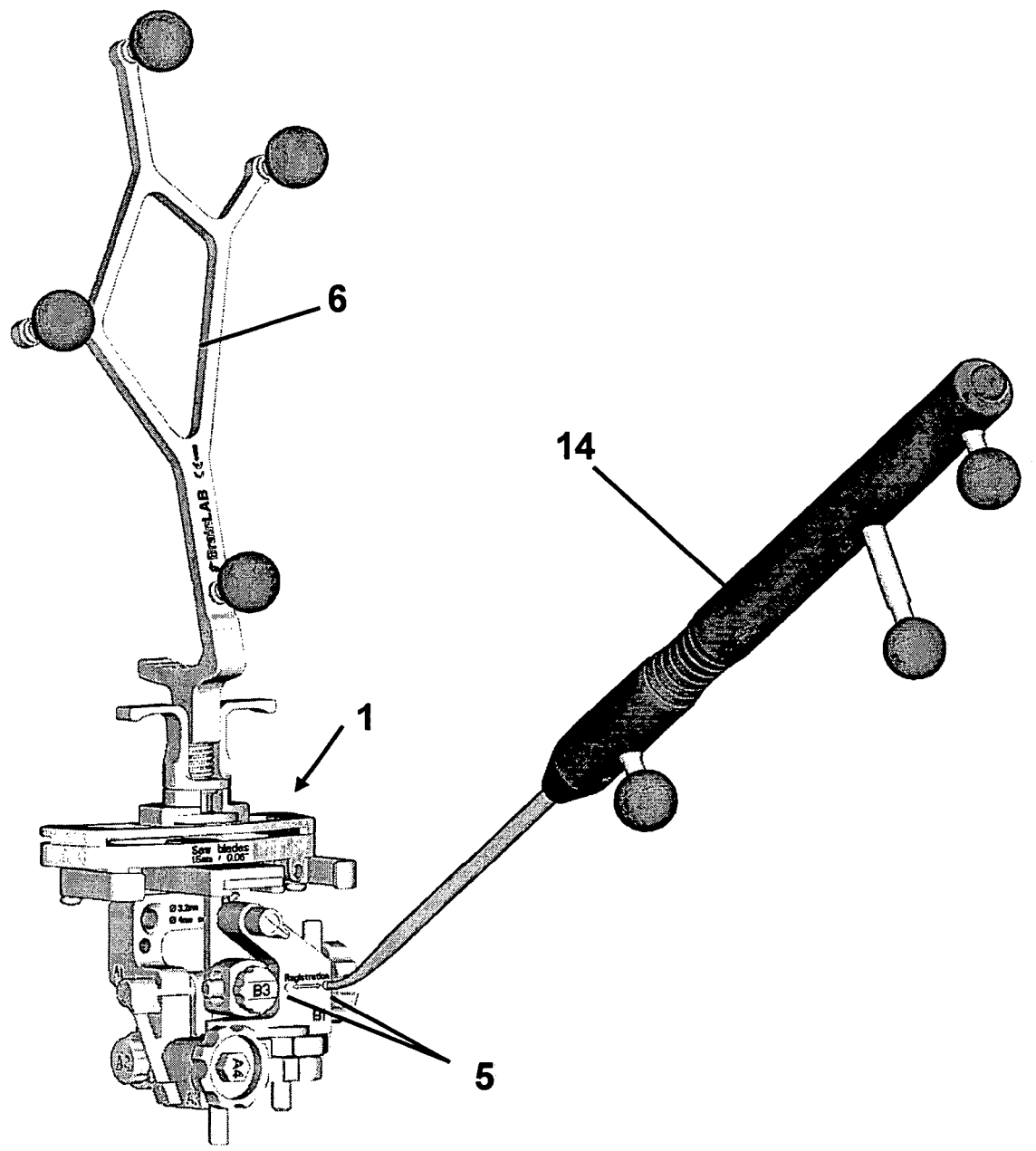
FIG. 10 illustrates an exemplary incision block while its spatial position is registered by means of a navigable pointer.

FIG. 10 shows the registration process of an incision block 1 including a registration element 5, which in the present example is two-dimensional. The depressions on the adjustment device are tapped using a pointer 14 which can be tracked by the navigation system and used to calculate the registration plane via a software algorithm.

Figure 11:
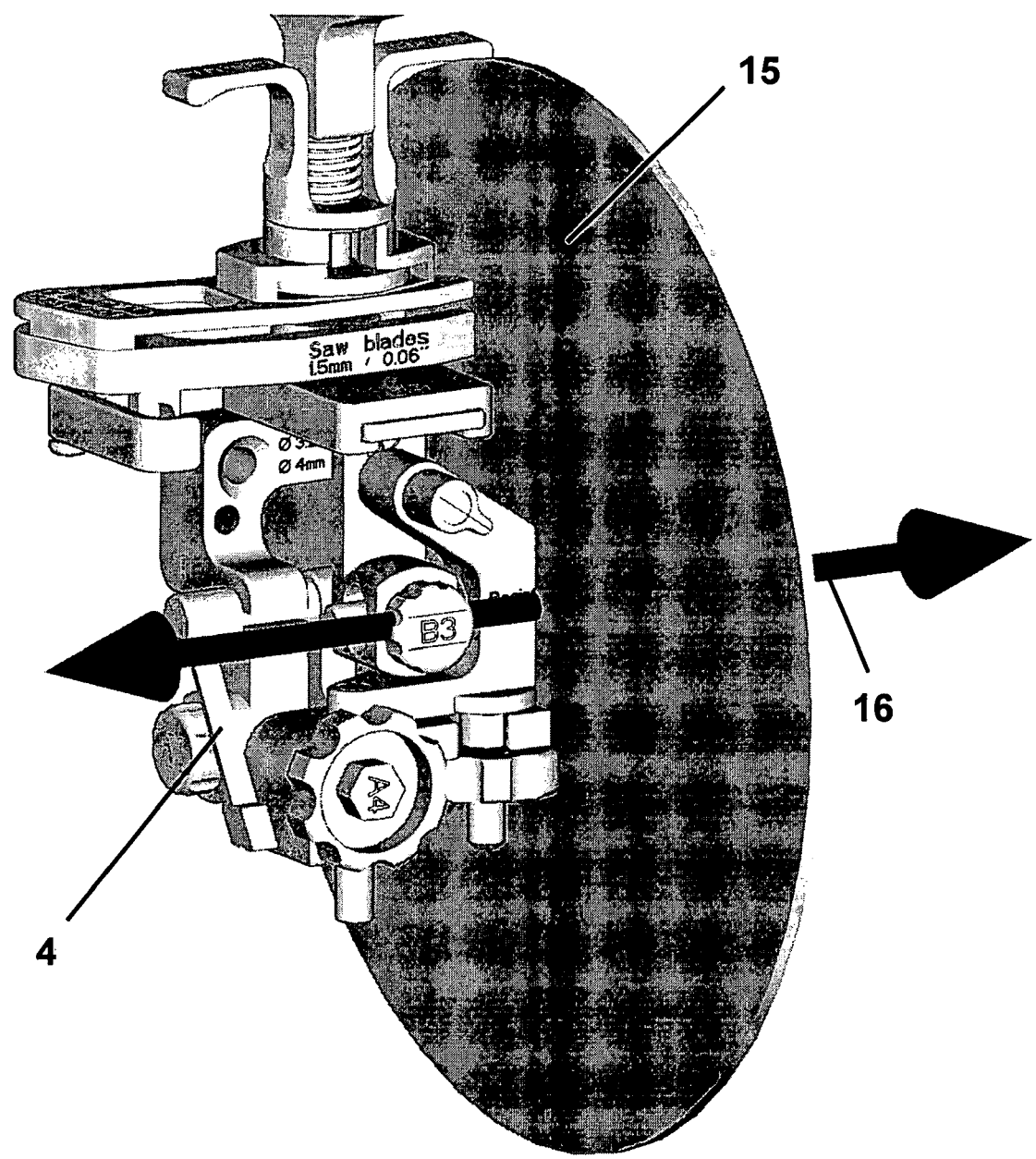
FIG. 11 illustrates an exemplary incision block with a registration plane whose normal vector is formed from the two registration points and which is simultaneously parallel to the plane of symmetry of the incision block.

FIG. 11 shows the registration plane 15 being formed, using the example of an incision block with a two-dimensional registration element. The connecting line of the registration points corresponds to the normal vector 16 of the registration plane, said vector being parallel to the plane of symmetry of the adjustment device 4 in the embodiment shown.

Figure 12:
FIG. 12 illustrates an exemplary screen output for guiding the user in registering the incision block.

FIG. 12 shows the representation of the instruction for the user in performing the registration process, wherein the spatial position of the adjustment device (here with a one-dimensional registration element) is determined with the aid of a navigated pointer.

Figure 13:
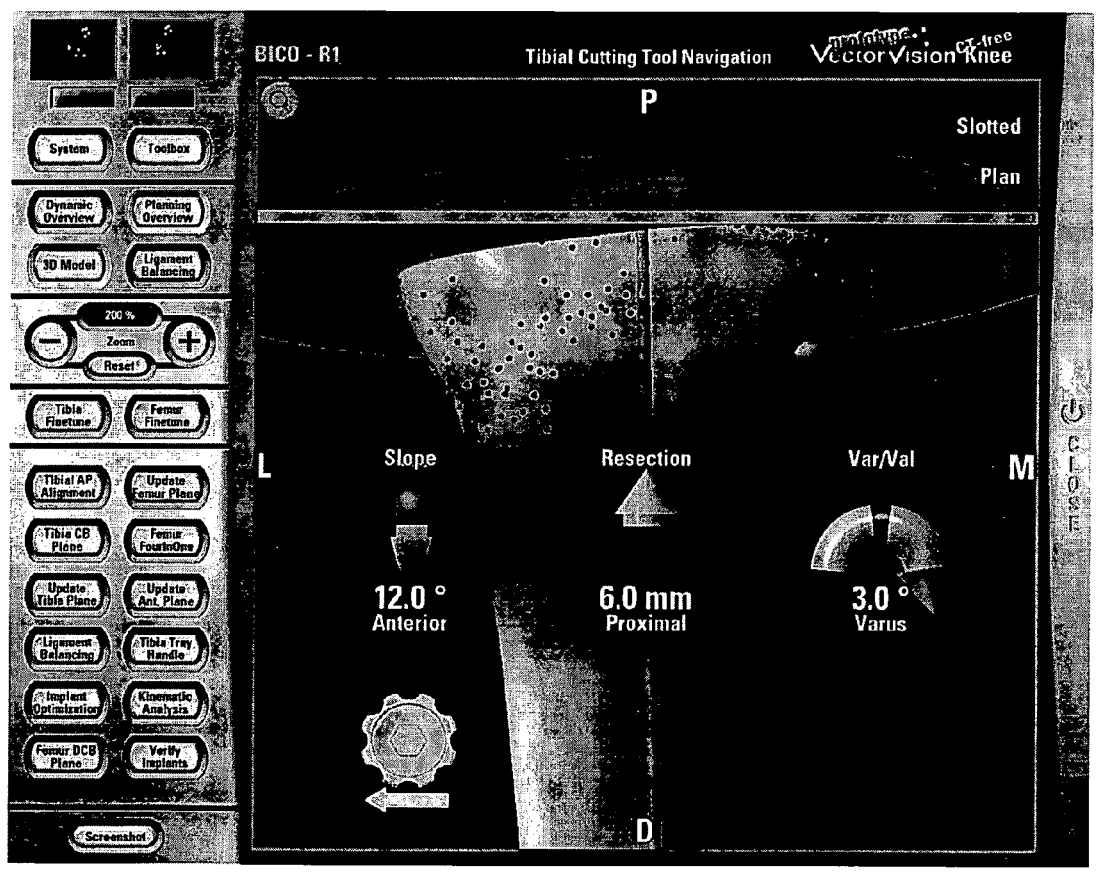
FIGS. 13-16 illustrate exemplary screen outputs for guiding the user in operating the adjustment device in the various degrees of freedom.

FIG. 13 shows one displaying option for guiding the user in setting the adjustment device with respect to the 'slope' degree of freedom of the incision plane. In accordance with the rotational movement necessary, a direction arrow is assigned to the corresponding setting medium, wherein this is indicated until the presets of the navigation system have been fulfilled by the user.

Figure 14:
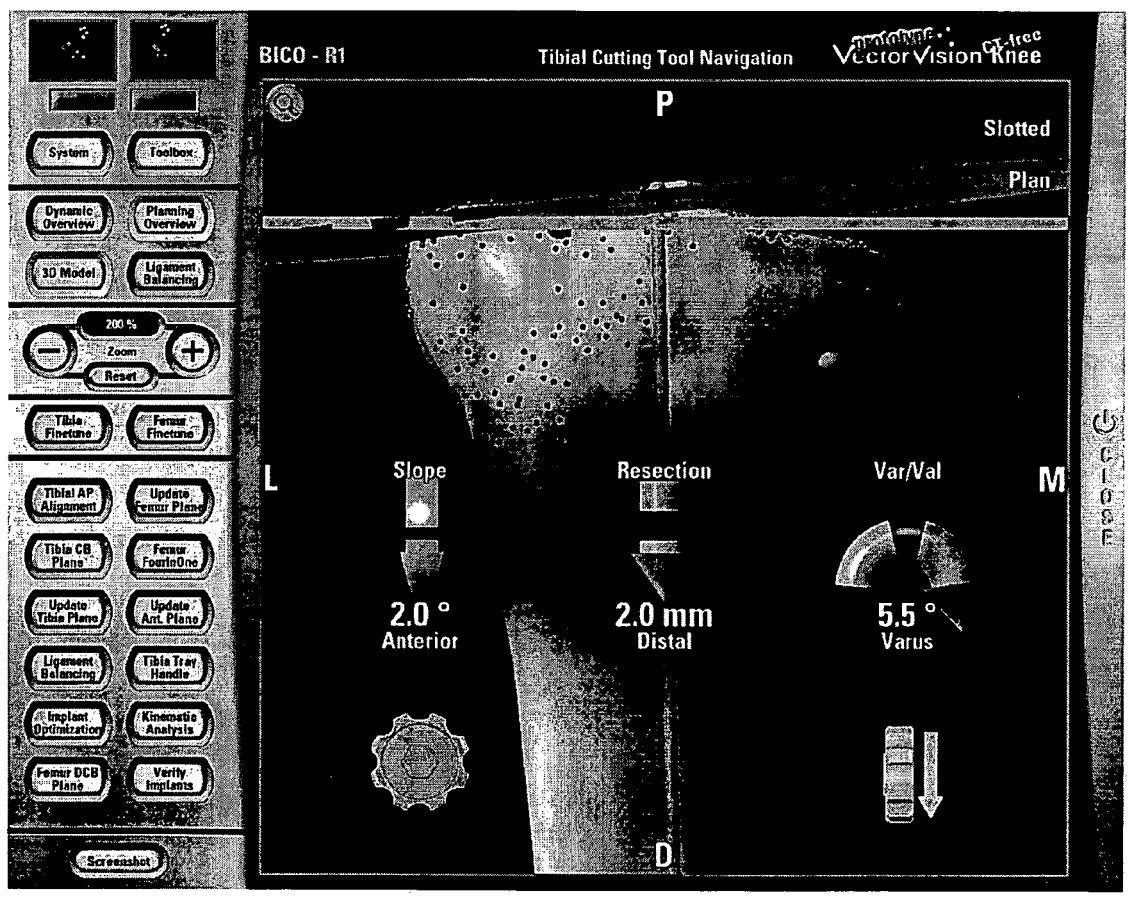

FIG. 14 shows one displaying option for guiding the user in setting the adjustment device with respect to the 'varus/valgus' degree of freedom of the incision plane. In accordance with the rotational movement necessary, a direction arrow is assigned to the corresponding setting medium, wherein this is indicated until the presets of the navigation system have been fulfilled by the user.

Figure 15:
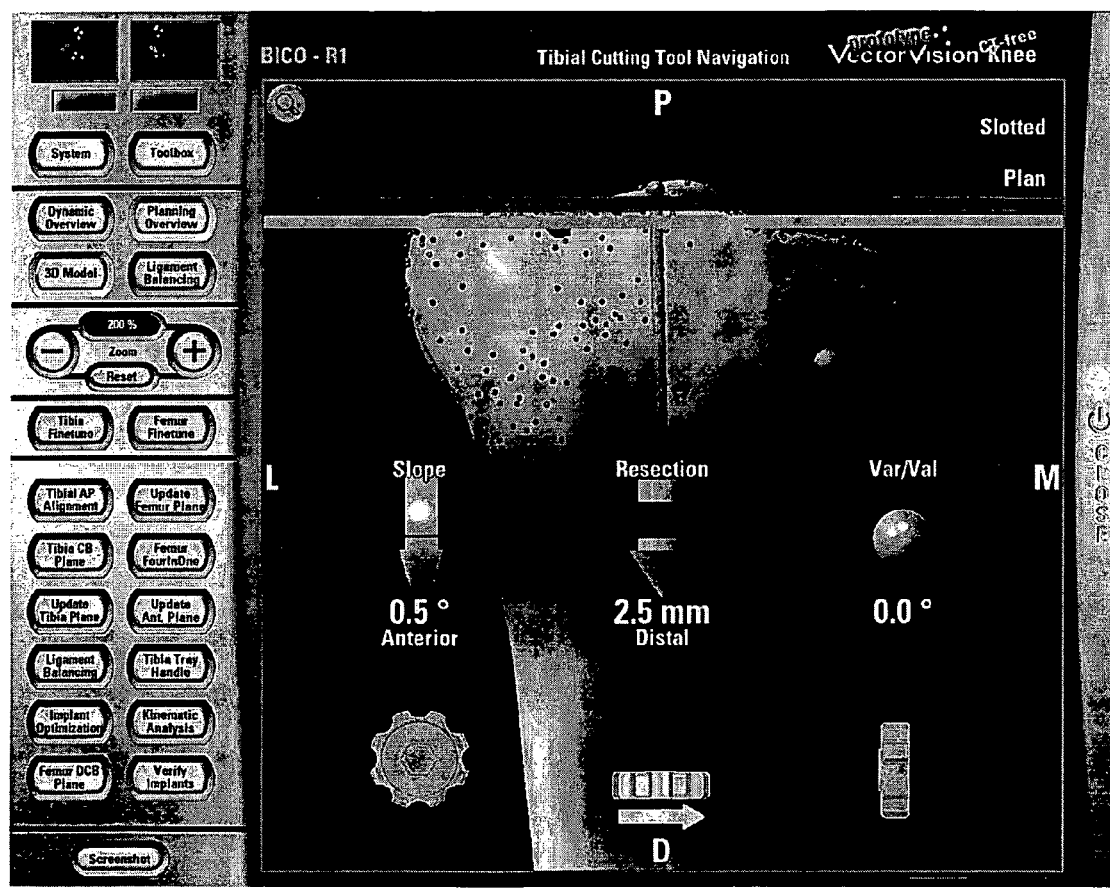

FIG. 15 shows one displaying option for guiding the user in setting the adjustment device with respect to the 'resection height' degree of freedom of the incision plane. In accordance with the rotational movement necessary, a direction arrow is assigned to the corresponding setting medium, wherein this is indicated until the presets of the navigation system have been fulfilled by the user.

Figure 16:
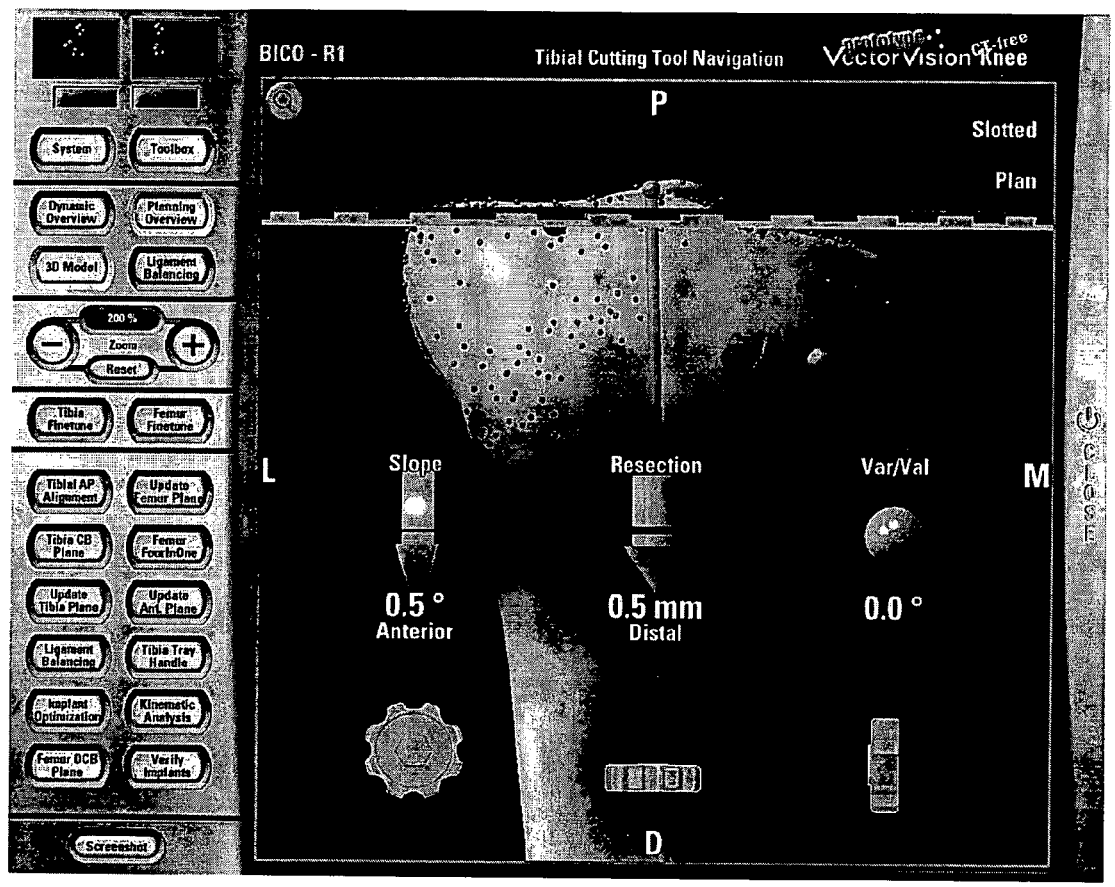

FIG. 16 shows one displaying option for the information for the user, once the adjusting process has been completed. All the setting media are indicated without any instructions for further rotating (no arrows are visible), since the actual incision plane corresponds to the target incision plane to the preset accuracy.

Figure 17:
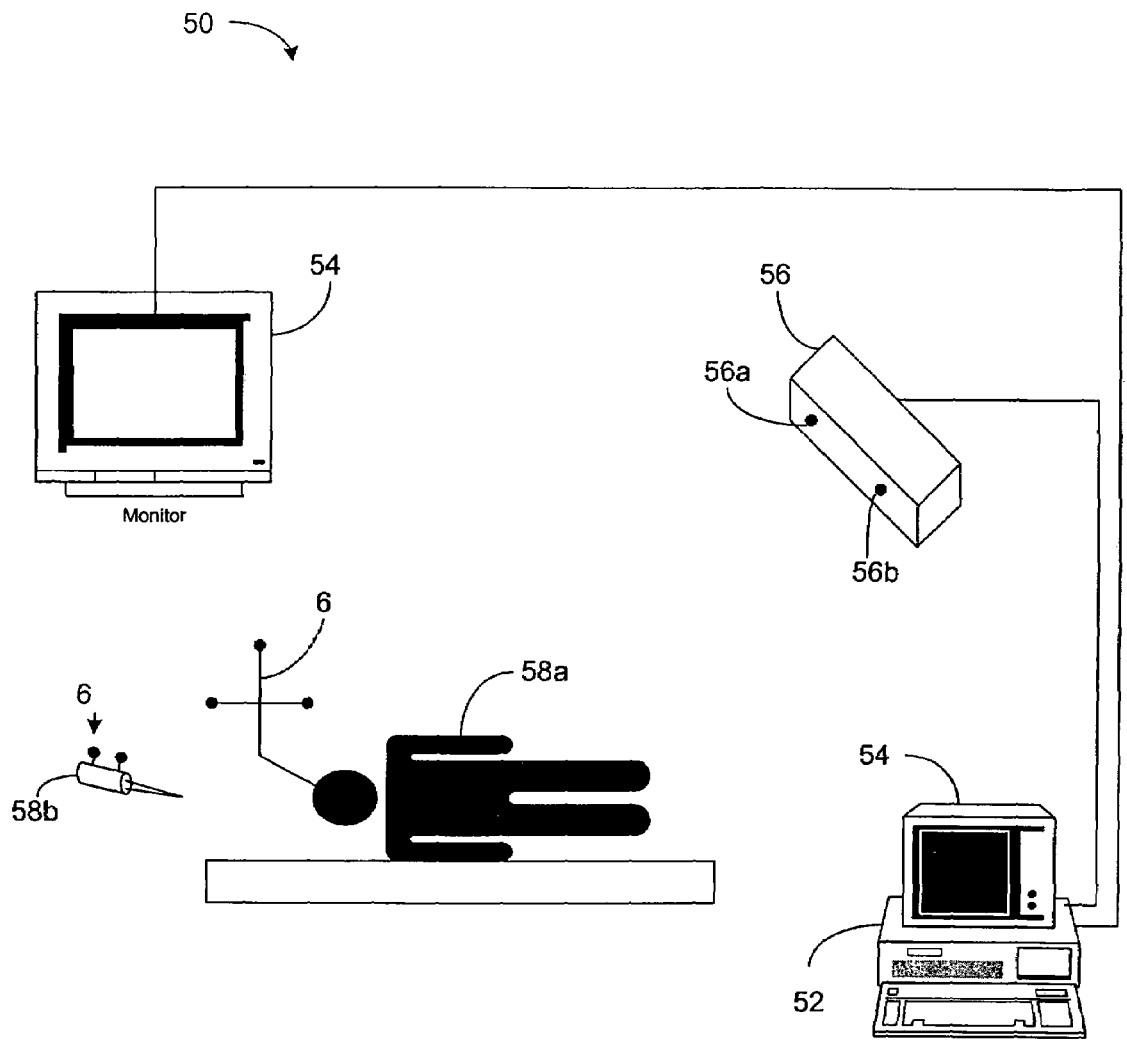
FIG. 17 illustrates exemplary navigation system that can be used with the invention.

FIG. 17 illustrates an exemplary medical navigation system 50 that may be used in carrying out the method. Navigation systems of various types are well known in the art and therefore will not be discussed in detail herein. Briefly, the navigation system 50 includes a computational unit 52, such as a computer that includes a processor and memory, one or more displays 54, and a camera system 56 (e.g., an infrared camera system). A reference device, such as the localization reference 6, is attached to an object of interest 58a, 58b (e.g., the bone, the incision guide, a patient's head, a reference pointer, etc.), and the camera system 56 ascertains the spatial position of the reference device (and thus the spatial position of the object). The spatial position is provided to the computational unit 52, which, via code residing on the computational unit, calculates a spatial position of the object.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A bone incision block, comprising:
    an incision guide that defines an incision plane;
    a localization reference rotatably attached to the incision guide, said localization reference enabling the incision plane to be spatially determined;
    a fastener for fastening to a bone;
    an adjustment device operatively coupled between the fastener and the incision guide, wherein the incision plane can be set relative to the bone via the adjustment device, and wherein adjusting movement of the incision guide relative to the fastener results in a corresponding movement of the localization reference; and
    a registration element for determining a spatial position of the adjustment device, said registration element independent from said localization reference.

2. The bone incision block according to claim 1, wherein the adjustment device comprises a setting device, said setting device enabling adjustment in height of the incision guide and adjustment in rotation of the incision guide around two non-parallel axes.

3. The bone incision block according to claim 2, wherein the adjustment device includes one setting medium for each of the adjustment in height and the adjustment in rotation.

4. The bone incision block according to claim 2, wherein the adjustment device has three degrees of freedom, and each setting medium comprises a hand wheel screw setting device.

5. The bone incision block according to claim 2, wherein the setting device are color coded and identified on a display based on the color coding.

6. The bone incision block according to claim 1, wherein the registration element includes an at least puncticular reference fixed to the adjustment device.

7. The bone incision block according to claim 1, wherein the registration element is arranged at a location characteristic of the individual bone incision block.

8. The bone incision block according to claim 1, wherein the registration element is arranged at a preset distance from the localization reference.

9. The bone incision block according to claim 1, wherein the incision guide and the localization reference can be arranged for various configurations at a defined presettable distance from the registration element.

10. The bone incision block according to claim 1, wherein the registration element is a depression at a point on the surface of the adjustment device.

11. The bone incision block according to claim 1, wherein the registration element has a two-dimensional extent.

12. The bone incision block according to claim 11, wherein the registration element is a bore at a point on the adjustment device or is formed by two depressions on the surface of the adjustment device, and the spatial position of the two elements can be ascertained using a navigated pointer.

13. The bone incision block according to claim 1, wherein the registration element includes a detection and display device for the relative angular position between the localization reference and the adjustment device.

14. The bone incision block according to claim 1, wherein the registration element includes a setting device for the relative angular position between the localization reference and the adjustment device that only allows and is lockable in predetermined and defined relative positions, and the set relative position can be indicated or read from a navigation system.

15. The bone incision block according to claim 1, wherein the localization reference comprises an elongated member rotatably attached to the incision guide, and wherein the localization reference is configured to rotate axially about a longitudinal axis of the elongated member.

* * * * *